United States Patent [19]

Wechsler et al.

[11] 4,269,730

[45] May 26, 1981

[54] SUBSTITUTED IMIDAZOLINE REACTIONS WITH CHLOROACETATE SALTS

[75] Inventors: Joseph R. Wechsler, Chicago; Thomas G. Baker, Wilmette; George T. Battaglini, Buffalo Grove; Frank L. Skradski, Grayslake, all of Ill.

[73] Assignee: Stepan Chemical Company, Northfield, Ill.

[21] Appl. No.: 70,537

[22] Filed: Aug. 28, 1979

Related U.S. Application Data

[63] Continuation-in-part of Ser. No. 901,713, May 1, 1978, abandoned.

[51] Int. Cl.³ ...................... B01F 17/28; B01F 17/30; C11D 1/10
[52] U.S. Cl. .................................. 252/356; 252/357; 252/546; 252/DIG. 6; 252/DIG. 7; 252/DIG. 13
[58] Field of Search ............... 252/356, 357, 89.1, 252/DIG. 7, 546; 260/404.5 R; 424/70

[56] References Cited

U.S. PATENT DOCUMENTS

| | | | |
|---|---|---|---|
| 2,961,451 | 11/1960 | Keough | 424/70 X |
| 2,970,160 | 1/1961 | Walker | 260/404.5 |
| 3,408,361 | 10/1968 | Mannheimer | 548/352 |
| 3,654,177 | 4/1972 | Foley | 252/356 |
| 4,121,009 | 10/1978 | Chakrabarti | 428/260 |

*Primary Examiner*—Richard D. Lovering
*Attorney, Agent, or Firm*—Hill, Van Santen, Steadman, Chiara & Simpson

[57] ABSTRACT

A process is provided for making amphoteric surfactant compositions from substituted imidazolines whereby such substituted imidazolines are reacted with chloroacetate salts and then hydrolyzed to open the imidazoline ring and produce a solution which is substantially completely free from cyclic groups. The product solutions are highly foamable and have low skin irritation and low eye irritation characteristics.

11 Claims, No Drawings

SUBSTITUTED IMIDAZOLINE REACTIONS WITH CHLOROACETATE SALTS

RELATED APPLICATION

This application is a continuation-in-part of my earlier filed U.S. application Ser. No. 901,713 filed May 1, 1978, and now abandoned.

BACKGROUND OF THE INVENTION

In the art of surfactants, it has been heretofore proposed that mild amphoteric surfactants could be prepared incorporating the imidazoline nucleus and containing quaternary ammonium complexes. An examination of commercially available surfactants alleged to be of this general type reveals that characteristically such are in the nature of complex physical mixtures which can have somewhat variable properties and which can contain minor components that can cause undesirable effects, such as skin and eye irritation, turbidity, poor storage characteristics, and the like.

Amphoteric surfactants derived from imidazoline have always heretofore been described as containing cyclic quaternary ammonium compounds. It is known in the art that quaternary ammonium compounds as a class of compounds tend to be skin and eye irritants. Thus for instance Arno Kluge, in an article on "The Properties of Quaternary Ammonium Salts and their Use in Cosmetic Products" published in Parfuemerie and Kosmetik 42, 341–6 (1961) describes alkylaromatic quaternary ammonium salts with alkyl groups having a chain length of from $C_{12}$ to $C_{16}$ as being skin irritants. Similarly J. M. Quack, in his article on "Quaternary Ammonium Compounds in Cosmetics" published in Cosmetics and Toiletries, vol. 91, pages 35–52, of February 1976, mentions that, although varying in their degree of toxicity and dermatologic insult depending on the alkyl chain length, quaternary ammonium compounds are classified in the literature of the art as being skin irritants.

Therefore, it would be desirable to have amphoteric surfactants derived from $C_{12}$–$C_{18}$ substituted imidazolines which are substantially free from quaternary ammonium salts. However, it is believed to be very difficult and probably impossible to make such amphoteric surfactants by following the prior art teachings. Thus for instance U.S. Pat. Nos. 2,781,354; 2,781,355; and 2,781,356 teach a method for making ampholytes from substituted imidazolines in which the end product is described as being primarily a cyclic quaternary ammonium hydroxide.

It has now been discovered that reactions of imidazoline derivatives in aqueous medium with neutral salts of chloroacetic acid and in absence of strong alkali form a cyclic betaine which is stable to hydrolysis at a pH below about 9. This cyclic betaine is a powerful surfactant which solubilizes the as yet unreacted alkyl imidazoline into the water layer. As a result of this dissolution the imidazoline ring opens up and straight chain amides are obtained which in turn react with the as yet unreacted chloroacetic salt to form amino acids which bring the pH further down, a property of these reaction conditions which protects the cyclic betaine from hydrolysis.

It has further been discovered that upon subsequent treatment with a strong alkali a straight chain compound is obtained from the cyclic betaine, said compound having a tertiary (trisubstituted) amide, in which one such substituent is a carboxy methyl group. This compound imparts what are now believed to be synergistic and even unique properties to the mixture of amphoteric compounds coexisting in a final product of this invention. Such properties are now believed to include one or more of enhanced solubility, foamability, and mildness. We were unable to obtain such a combination of properties either by the synthesis of ampholytes from the precursor amide directly, or by preparing ampholytes from imidazoline by using the currently proposed methods as shown in the prior art.

Product compositions of this invention prepared as herein described are clear solutions, yellow straw in color.

A further and very significant feature of this invention is the circumstance that, if the process step sequence of this invention is not followed (for example, if the first and second process steps are not sequentially practiced, but are instead simultaneously practiced), the storage of stable product compositions of this invention are not achieved and clouding upon storage of such other composition is characteristically observed.

There is a need in the art for amphoteric surfactants which are derived from substituted imidazolines, which are highly foamable (as can be considered characteristic of such amphoteric surfactants), which have minimal skin irritating and eye irritating characteristics, and wherein a carboxymethyl or a hydroxyethyl group is attached to the amide nitrogen (making tertiary amide compounds). Concurrently, of course, methods for making such improved amphoteric surfactants are likewise needed.

BRIEF SUMMARY OF THE INVENTION

There has now been discovered a new and very useful process for preparing amphoteric surfactants which overcome the above indicated problems heretofore associated with amphoteric surfactants derived from imidazoline. The process leads to a new and very useful class of amphoteric surfactant compositions derived from imidazoline.

In one aspect, the present invention relates to a technique for making acyclic amphoteric surfactants derived from imidazoline which are substantially free from cyclic quaternary ammonium salts.

In another aspect, the present invention aims to provide an improved amphoteric surfactant composition derived from imidazoline wherein a carboxymethyl or a hydroxyethyl group is attached to the amide nitrogen.

Other and further aspects, aims, advantages, objects, features, utilities and the like will be apparent to those skilled in the art from the present description.

DETAILED DESCRIPTION

Imidazoline starting materials useful in the practice of this invention are characterized by the general formula:

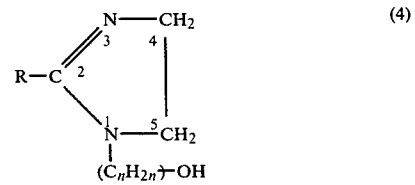

(4)

where:

R is an aliphatic radical containing from about 5 to 19 carbon atoms per molecule, and n is a positive whole number of from 2 to 4, inclusive.

Preferably, R is an aliphatic radical containing from 11 to 13 carbon atoms per molecule, as n is 2.

Because of the known methods of making compounds of formula (4) and because of the known utilities for such (including use in the practice of the present invention), commonly any given batch comprised of starting compounds of formula (4) will contain mixtures of different R radicals within the ranges above defined. Thus, in one more preferred starting material, R is a residue from lauric acid ester and so R is an alkyl radical of 11 carbon atoms. In another more preferred starting material batch, R is a mixture of saturated and unsaturated aliphatic radicals derived from coconut oil or similar natural oil sources and here each R in such a mixture contains from about 11 to 17 carbon atoms. In still another more preferred starting material batch, R is a mixture of alkyl radicals derived from a saturated portion of coconut oil or similar natural vegetable oil sources and here each R of such a mixture contains from about 11 to 13 carbon atoms.

The formula (4) compounds useful in this invention should be initially in a substantially pure form. By the term "substantially pure" reference is had to a batch of formula (4) compound (which may be a mixture of compounds, if desired, wherein R varies, as explained) wherein the formula (4) compound constitutes at least about 92 weight percent thereof with the balance up to 100 weight percent thereof being comprised of not more than about 3 weight percent of aminoethyl ethanol amine, not more than about 2 weight percent of byproduct ester having an infrared peak at 5.75 microns, not more than about 5 weight percent aliphatic monoamide, having an infrared peak at 6.0 microns, and not more than about 1.5 weight percent of all other organic and inorganic components combined weight. Specifically, the starting formula (4) compounds should be substantailly free of organic diamides, and should contain not more than about 1 weight percent of catalyst derived soap, such as an alkali salt of a precursor fatty acid containing metal material, or derived material used in forming the starting imidazoline of formula (4).

Any convenient procedure can be employed to prepare imidazoline starting materials of formula (4), as those skilled in the art will appreciate. However, it is preferred to use a process for preparing such imidazoline starting materials such as is disclosed in our copending application filed on May 1, 1978 as U.S. Ser. No. 901,713, now abandoned, because a material so obtained contains, if any, less than about 2 percent byproduct ester and is substantially free from diamide, and also the material is at least about 95 percent pure.

In practicing the process of the present invention, one first heats an agitated mixture comprised of at least one substantially pure compound of formula (4), at least one chloroacetate salt, and water. Preferably the chloroacetate salt is in aqueous solution before admixing. Any convenient means for agitation can be employed with the amount of agitation used being sufficient to intermix the starting component. Such an intermixing is desirable since initially the starting components are not miscible in one another.

Chloroacetate salts usable in the practice of the present invention are characteristically those wherein the cationic portion thereof is selected from the group consisting of alkali ions. One presently preferred chloroacetate salt is sodium chloroacetate. Preferably, chloroacetate salts used in the practice of this invention are in a highly purified form (that is, they contain not more than about 1.5 weight percent impurities). Thus, commercial grades of chloroacetate salts can be used if desired.

The heating of such a starting mixture is conducted at a temperature ranging from about 70° to 80° C. for a time sufficient to bring the pH of the reacting medium down to between 7.5 and 8.5. During this period the nitrogen in the three position of the formula (4) reacts with the chloroacetate salt so as to form a cyclic betaine in sufficient amount to solubilize the unreacted organic phase into the water phase, thus allowing ring opening to occur. The cyclic betaine so obtained is quite stable at a pH below about 9. During this first period of heating the pH drops rapidly from about 11.5 to about 8.5 and then steadily to about 7.5, a fact which protects the structure of the cyclic betaine.

The dominant reactions believed to take place during this first period of heating are the following:

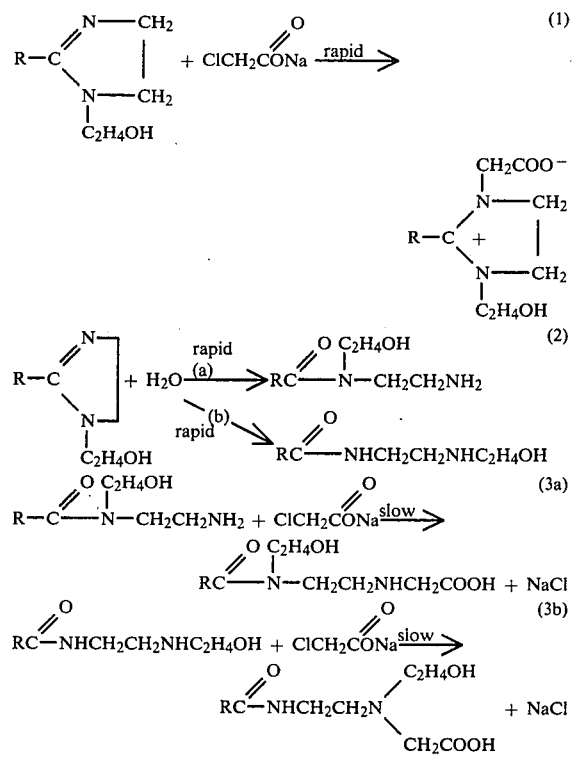

In the starting mixture, the amount of water present is such that the mixture comprises on a 100 weight percent total mixture basis from about 20 to 50 weight percent solids with the balance up to 100 weight percent thereof being water. Also, in such mixture, the quantity of chloroacetate salt is such that the mixture contains an equivalent of from about 1.0 to 2.5 moles of such chloroacetate salt for each mole of formula (4) compound. All of the chloroacetate salt may be initially present with the formula (4) compound at the initiation of such heating; however, the chloroacetate salt can also be added gradually. The preferred method of contacting is to bring the reactants into the reaction zone simultaneously in a continuous manner so that neither one of the reactants would be in overwhelming molecular excess at any time during contacting. The reactions cited in equations 1 through 3 are given for illustration purposes. Knowledge of chemical theory and experiments described hereunder indicate that there is a high probability that these reactions will take place in the manner stated above.

It is known (see for instance Jan Torquist in "Chemical and Physical Applications for Surface Active Substances", Asinger, vol. I page 387) that the nitrogen in the 3 position of the compound of formula (4) is more basic than that in the 1 position thereof so that it is more likely to react with the organic chloride.

There is no harm in extending the duration of the first heating step because the main effect of such extension is to produce more reaction between the linear amines in solution and the (as yet) unreacted NaOOCCH$_2$Cl so as to form linear products which are the desired form of the product within the scope of this invention. Typically, however, it has been found that about one hour of heating under the conditions specified above is sufficient to complete this step.

Thereafter, one gradually mixes with the resulting reactant mixture from about 1.0 to 2.5 moles, corresponding to the total equivalent molar amount of chloroacetate salt initially added to such reactant mixture, of a base selected from the group consisting of alkali metal hydroxides. The effect of said strong base in the reaction mixture is to cause ring opening of the cyclic betaines so that complete hydrolysis can be achieved in a relatively short time; to neutralize any free carboxylic groups; and to complete the reaction between linear amidoamines and chloroacetic salts to form linear ampholytes.

After such mixing of base with resulting reactant mixture is completed, a second heating of the resulting reactant mixture with such base is commenced. Such second heating is conducted at a temperature of from about 70° to 80° C. for a time at least sufficient to open all of the cyclic structures present in the mixture and to complete the reaction between ClCH$_2$COONa and available primary and secondary amine groups. A clear aqueous solution of linear amphoteric compounds results, normally having a pH of about 8.5–11.5. This solution is substantilly completely free from cyclic groups, as can easily be attested for example, by ultra violet analysis, which shows an absence of the peak characteristic for the imidazoline structure. Any convenient analytical technique can be used.

The reactions taking place during the second heating step are theorized to be mainly the following:

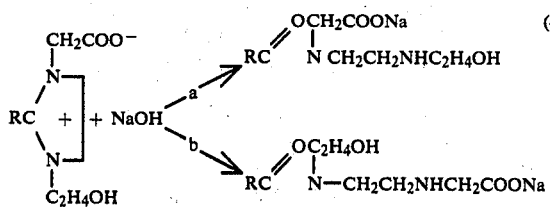

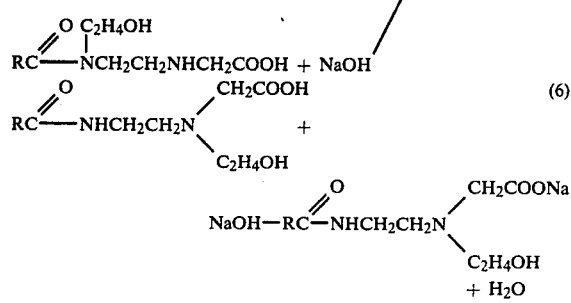

And, if more than one mole ClCH$_2$COONa per mole imidazoline was used:

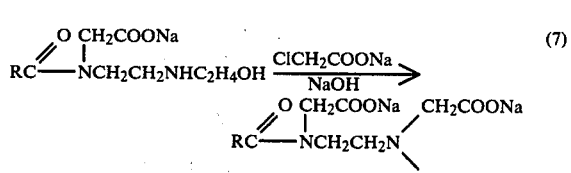

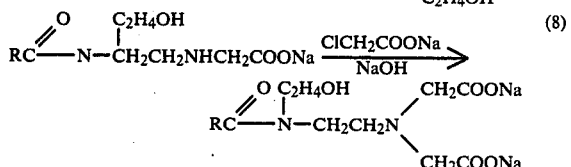

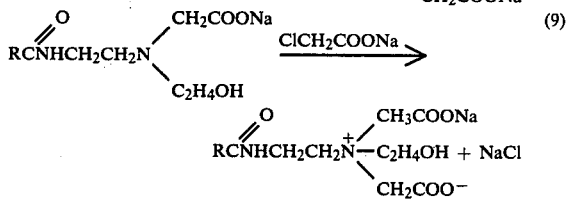

The experiment described hereunder is one of the experiments carried out for the purpose of elucidating the mechanism of the reaction:

One mole (268 grams) of pure (99.9%) lauric imidazoline was reacted with two moles (233 grams) of sodium chloroacetate dissolved in 1060 grams water at 75° C. for 1½ hours. Samples were withdrawn at 15 minute intervals and analyzed for NaCl content and for content of compounds of cyclic structure by ultra violet spectra. Then two moles of 50% NaOH were introduced over a period of ½ hour, and the resulting mixture was further digested for 4 hours at 75° C., all the while taking samples at regular intervals and analyzing them as described above. Results are shown in Table I.

Further analysis on the final product revealed that it contained 0.15 meq/gm linear betaine, and a maximum of 1% sodium glycolate (if any).

Table II shows the results obtained in another experiment which was run under identical conditions, except that only 1 mole sodium chloroacetate was used, and the NaOH addition was started after 60 minutes.

TABLE I

| | (All Data in Mole Percentages) | | | | | | | | | | | | | |
|---|---|---|---|---|---|---|---|---|---|---|---|---|---|---|
| Time (minutes) | 0 | 5 | 12 | 17 | 22 | 42 | 63 | 78 | 98 | 114 | 128 | 144 | 158 | 220 | 250 |
| 2:1 Ratio | | | | | | | | | | | | | | | |
| Cyclic Betaine | | 1.6 | 11.2 | 26.9 | 25.2 | 24.5 | 23.5 | 23.6 | 23.7 | 23.1 | 15.3 | — | | | |

TABLE I-continued

| | (All Data in Mole Percentages) | | | | | | | | | | | | | |
|---|---|---|---|---|---|---|---|---|---|---|---|---|---|---|
| Time (minutes) | 0 | 5 | 12 | 17 | 22 | 42 | 63 | 78 | 98 | 114 | 128 | 144 | 158 | 220 | 250 |
| Imidazoline | 36.9 | 28.1 | 9.5 | — | — | — | — | — | — | | | | | | |
| Amide | 61.5 | 60.7 | 63.7 | 44.5 | 34.83 | 25.0 | 20.9 | 16.4 | 12.9 | 0.3 | — | | | | |
| Amino Acid | — | — | — | 30.4 | 40.7 | 51.5 | 55.5 | 59.9 | 63.9 | — | — | | | | |
| Ampholytes-monocarboxylic | | | | | | | | | | 84.4 | 55.4 | 44.2 | 13.0 | 6.6 | 1.5 |
| Ampholytes-di and tricarboxylic | | | | | | | | | | | 44.6 | 55.8 | 87.0 | 93.4 | 98.5 |

TABLE II

| | (All Data in Mole Percentages) | | | | | | | | | | |
|---|---|---|---|---|---|---|---|---|---|---|---|
| Time (minutes) | 0 | 5 | 22 | 42 | 70 | 80 | 91 | 101 | 120 | 180 | 220 |
| 1:1 Ratio | | | | | | | | | | | |
| Cyclic Betaine | 3.0 | 3.9 | 22.1 | 20.4 | 19.6 | 15.8 | 6.9 | 0.5 | — | | |
| Imidazoline | 84.6 | 64.4 | — | — | — | — | — | — | — | | |
| Amide | 12.4 | 31.7 | 63.5 | 46.3 | 33.2 | 28.9 | 24.5 | 19.8 | 8.6 | | |
| Amino Acid | — | — | 14.4 | 33.3 | 47.2 | 23.6 | 0.8 | — | — | 2.0 | 0 |
| Ampholytes-monocarboxylic | — | — | — | — | — | 32.3 | 67.8 | 79.8 | 91.4 | 98.0 | 100 |

We have found that although the hydrolysis of imidazoline during the first heating period, as illustrated in equations (3) above, favors route (3b) over (3a), still a sizable amount of product (3a) is formed. We have also found that, as illustrated in equations (4) and (5), ampholytes having a tertiary amide function are obtained not only from the cyclic betaine, as shown in equations (4a) and (4b), but also from said hydrolysis of the imidazoline, as shown in reaction (5). Furthermore, we have found that, as it is shown in Tables I and II, the amount of cyclic betaine prior to the addition of NaOH stabilizes at about 20 to 24 mole percentage.

Therefore, the combined sources of tertiary amide containing ampholytes, i.e. the cyclic betaine as well as the reaction (2a), are conducive to the formation of a final combination of amphoteric compounds in which at least 25% of such compounds contain a tertiary amide structure.

In a presently preferred mode of practicing the process of the present invention, the formula (4) compound is charged to the zone of first heating as a starting composition of substantially pure formula (4) compound. Such a starting composition preferably consists essentially on a 100 weight percent total weight basis of from about 92 to 99.5 weight percent of formula (4) compound, or compounds as the case may be, from about 0.5 to 3 percent of aminoethyl lower alkanol amine, from 0 to no more than about 2 weight percent of a byproduct ester, a common impurity with commercial imidazoline, detected by a characteristic infrared peak at 5.75 microns, and from 0 to about 5 weight percent of an aliphatic monoamide detected by a characteristic infrared peak at 6 microns. More preferably, such a starting imidazoline composition contains, on a 100 weight percent total weight basis, from about 97 to 99.5 weight percent of formula (4) compound wherein n is 2, from about 0.5 to 1 weight percent of aminoethyl ethanol amine, from 0 to about 2 weight percent of such monoamide, and substantially no ester impurity.

Compositions produced by the process above described are preferably characterized by having a skin irritation of not more than about 1.0/8.0 on albino rabbits as determined by the Draize et al procedure. Also, such a composition preferably has an eye irritation of not more than about 15/110.0 on albino rabbits by the Draize et al procedure.

In addition, such a product composition has a foamability such that a Ross-Miles test conducted with a 0.10% active aqueous solution in distilled water produces a foam height of at least about 16 centimeters.

In addition, a composition produced by the process of this invention is further characterized by
 (A) having a stability such that said composition remains a clear solution after at least about 7 days of storage at 5° C.,
 (B) containing an amphoteric compound having a tertiary amide function, said amphoteric compound being present in the amount of at least 25% by weight of total ampholyte,
 (C) containing an amphoteric compound having a tertiary amide function in which one of the substituents on the tertiary nitrogen is a carboxymethyl group, said amphoteric compound being present in the amount of at least 10% by weight of total ampholyte.

Preferred product compositions involve the use of a starting formula (4) compound wherein n is 2. In one more preferred product, R is a residue from a lauric acid ester and hence is an alkyl radical of 11 carbon atoms. In another more preferred composition R is a mixture of saturated and unsaturated aliphatic radicals derived from coconut oil or similar natural oil source and here each R contains from about 5 to 17 carbon atoms. In still another more preferred product composition, R is a mixture of alkyl radicals derived from a middle portion of coconut oil or similar natural vegetable oil source and in such a situation R contains from about 11 to 13 carbon atoms.

We are at this time as yet unable to identify the structure of the ester impurity above referenced, which should not exceed a maximum amount of about 2 weight percent in a starting composition of formula (4) compound used in the practice of the present invention.

The structure of the aliphatic monoamide, above referenced, which should not exceed a maximum amount of about 5 weight percent in a starting composition of formula (4) compound used in the practice of the present invention, is believed to be predominantly of the following structure:

$$RCONHCH_2CH_2NHC_2H_4OH \tag{15}$$

It has been found that, if such ester impurity exceeds about 2% by weight of the starting imidazoline, the resulting ampholyte will have a reduced foam height. A similar result is observed when said starting imidazoline contains more than about 5% of said monoamide. We can verify that no imidazoline ring structure is present in a composition produced by the process of this invention, as demonstrated by ultra violet analysis, for example.

Some differences in product compositional characteristics are achieved by varying the mole ratio of chloroacetate salt to formula (4) compound employed during the initial or first heating step as above described.

The ampholytes that are produced by following the teachings of this patent are extremely mild and non-irritating to both skin and eyes, exhibit high foaming properties, low toxicity, excellent compatibility with other ionic and nonionic surfactants, excellent stability, and are biodegradable. The properties of these ampholytes make them very suitable for use in products ranging from cosmetics to industrial applications. Certain of these ampholytes are particularly suitable for formulating non-irritating shampoos and detergents.

As indicated in reactions 1 through 3 above, the composition of the reactant mixture resulting from the first heating step is theorized to consist of a mixture of cyclic betaine and open chain compounds. The weight ratio between these respective compound types depends upon the difference between the relative rates of reaction of chloroacetate with formula (4) compound on the one hand compared to the rate of hydrolysis of the reaction product of formula (4) compound with chloroacetate.

As indicated in reactions 4 through 9 above, the composition of a product produced by the process of the present invention is generally a mixture of different open chain structures, some containing a tertiary amide group, which it is theorized imparts enhanced solubility and mildness to the product.

One can attempt to prepare such linear ampholytes directly from the amide precursor. Such amides are easily obtained by reacting for instance a fatty methyl ester with a suitable diamine, such as aminoethyl ethanol amine, at moderate temperature, so as to drive the reaction to completion without dehydrating the obtained amide. Such amide will readily react with sodium chloroacetate in presence of alkali to form amphoteric compounds. However, amides so obtained are likely to contain a substantial amount of diamide, which is an inert material insoluble in water.

EMBODIMENTS

The present invention is further illustrated by reference to the following examples. Those skilled in the art will appreciate that other and further embodiments are obvious and within the spirit and scope of this invention from the teachings of these present examples taken with the accompanying specification.

In the following examples 1 through 4 there is employed as a starting imidazoline composition comprised on a 100 weight percent basis of at least 97 weight percent substituted imidazoline, not more than 1 weight percent byproduct ester, not more than 1 weight percent aminoethyl ethanol amine, not more than 2% alkylamido amine and substantially no diamide. This product is prepared by the teachings of our co-pending application filed on May 1, 1978 as U.S. Ser. No. 901,713, now abandoned.

In the following examples, unless otherwise specifically stated, each product composition of this invention has the preferred low skin and eye irritation properties indicated above, and each such composition has a foamability of at least about 16 centimeters by the Ross-Miles test procedure, has a stability such that said composition remains a clear solution after at least about 7 days of storage at 5° C.

EXAMPLE A 214 g. (1.0 mole) of methyl laurate is weighted into a reaction flask and mixed with 156 g. (1.5 moles) of aminoethyl ethanol amine, which has been purified by stripping off a first fraction of about 5 weight percent whereby the content of ethylene diamine was reduced from 250 ppm to about 5 ppm. To this mixture is added 2 g. of a 25% solution of $NaOCH_3$ in methanol and the mixture is heated with agitation while bubbling dry nitrogen into the reaction zone. When the temperature reaches about 90° C. methanol starts distilling out of the reaction zone, and the rate of distillation increases as the temperature is brought to 165° C. After one hour at 165° C. a sample is withdrawn and an infrared spectrum of that sample shows that there is still 5.6% methyl ester present. After one additional hour at 165° C. an infrared spectrum and a determination of unreacted aminoethyl ethanol amine (hereinafter designated as AEEA) give the following composition:

methyl ester: nil
amide: 60.5%
imidazoline: 24.3%
excess AEEA: 15.2%

The pressure in the reaction flask is now gradually reduced to 150 mm Hg over a period of about 10 minutes, care being taken to avoid any contact between reactants and air, which would cause rapid and severe darkening of the product, while at the same time the temperature in the reaction zone is raised to 200° C. The reactants are kept at that temperature for a period of two hours while the pressure in the reaction zone is gradually reduced at a rate such that a pressure of 60 mm Hg is reached after the elapse of two hours from the time of reaching the temperature of 200° C. in the reaction zone. At this stage the composition of the reactants is found to be:

ester: nil
amide: 3.3%
imidazoline: 92.1%
AEEA: 4.6%

Now the temperature is gradually reduced to 175° C. while the pressure is also reduced gradually to 25 mm Hg over a period of one hour, at the end of which period a complete analysis shows the following:

ester: nil
amide: 1.5%
imidazoline: 95.5%
AEEA: 2.2%
Na laurate: 0.75%
free alkali: nil Upon cooling to room temperature without any contact with air the final material is obtained as a straw colored clear liquid which crystallizes after standing overnight to a white solid melting at 43° to 46° C. The yield is 274 g.

EXAMPLE B

The process of Example A is repeated except that methyl laurate is replaced with a mixture of methyl esters of a composition corresponding to the molecular distribution of coconut oil, from which the lower fractions of $C_6$, $C_8$, and $C_{10}$ methyl esters have been removed. 231 g. of said mixture of methyl esters (1.0 mole) is reacted with 156 g. AEEA (1.5 moles) and 2 g. of a 25% solution of NaOCH$_3$ in methanol by using the same procedure as described in Example 1. The final material is a straw colored liquid weighing 283 g. and having the following composition:
- ester: 0.3%
- amide: 1.2%
- imidazoline: 96.1%
- AEEA: 1.6%
- Na cocoate: 0.78%

Unlike the material described in Example A, this liquid does not solidify on standing at room temperature.

EXAMPLE 1

175 g. of sodium chloroacetate (1.5 moles) is dissolved in 724 g. water and the obtained solution is placed in a dropping funnel. 281 g (1 mole) of an imidazoline material obtained by a method described in Example A is placed into a second dropping funnel. The materials are released from said funnels into a 2 liter reaction flask at a rate such that the solution in the first dropping funnel is flowing about 3 times faster into said flask than the material in the second dropping funnel, while the material accumulating in the flask is maintained at a temperature of 75° C. by heating with a heating mantle, and homogenized by gentle agitation. Total time of addition takes about 30 minutes. Thereafter the material is maintained at 75° C. for one additional hour. At this point 120 g. of a 50% solution of NaOH (1.5 moles) 100 percent basis in water is gradually introduced into the obtained mixture over a period of about 20 minutes, while maintaining said mixture at 75° C. When all the alkali solution had been added the obtained mixture is maintained at 75° C. for an additional two hours. At this point an ultra violet analysis confirms the absence of heterocyclic compounds in the mixture. There is obtained 1300 g. of a clear, pale colored product, comprising the following ingredients:
- imidazoline derived acyclic ampholyte: 385 g.
- aminoethyl ethanol amine derived ampholyte: 26.5 g.
- monoamide derived ampholyte: 8 g.
- NaCl byproduct: 87.8 g.

A sample of this product is placed in a refrigerator at 5° C. and is found to remain perfectly clear for at least 7 days. A Ross-Miles test performed at 25° C. with a 0.1% active solution in water of this product produces a foam height of 17.5 cm which does not drop below 17.0 cm after 5 minutes. A rabbit eye and skin irritancy test performed according to Draize et al gives results of 15/110 and 1.0/8.0 respectively.

EXAMPLE 2

268 g. (2.3 moles) of sodium chloroacetate is dissolved in 1363 g. water and the obtained solution is placed into a dropping funnel. 281 g (1 mole) of an imidazoline material obtained by a process described in example A is placed into a second dropping funnel. The materials are released from said funnels into a 3 liter reaction flask at a rate such that the solution in the first dropping funnel is flowing about 6 times faster into said flask than the material in the second dropping funnel, while the materials accumulating in the reaction flask are maintained at 75° C. under a mild agitation. Total time of this addition takes about 40 minutes. Thereafter the material is maintained at a temperature of 75° C. for one additional hour. At this point 184 g. of a 50% solution of NaOH (2.3 moles) in water is gradually introduced into the obtained mixture over a period of about 30 minutes, while maintaining said mixture at 75° C. When all the alkali solution had been introduced into the reaction flask the obtained mixture is maintained at 75° C. for an additional two hours under gentle agitation. At this point an ultra violet analysis confirms the absence of heterocyclic compounds in the mixture. There is obtained 2096 g. of a clear, pale colored product which contains the following ingredients:
- imidazoline derived acyclic ampholyte: 467 g.
- aminoethyl ethanol amine derived ampholyte: 20.5 g.
- monoamide derived ampholyte: 6.8 g.
- NaCl byproduct: 134.5 g.

A representative sample of said product is placed in a refrigerator at 5° C. and observed to remain perfectly clear for at least 7 days. A Ross-Miles test performed at 25° C. with a 0.1% active solution of this product produces a foam height of 19 cm which does not drop below 18.5 cm after 5 minutes. A rabbit eye and skin irritancy test performed according to Draize et al gives results of 13/110 and 1.0/8.0 respectively.

EXAMPLE 3

The process described in example 2 is repeated with the difference that the imidazoline material therein is replaced with an imidazoline material obtained by a process described in example B. The final amphoteric product so obtained has properties similar to those of the product obtained by the method described in example 2, except that the foam height is 16 cm (16 cm after 5 minutes) and the above described irritancy tests are 9/110 and 0.6/8.0 respectively.

EXAMPLE 4

The process described in example 2 is repeated with the difference that the amount of sodium chloroacetate used is augmented to 350 g. (3.0 moles). The obtained product is submitted to a rabbit skin and eye irritancy test and the results of said test show an eye irritancy of 37/110 and a skin irritancy of 2.4/8.0, indicating that when a substantially higher content of acyclic quaternary ammonium compounds are formed, the irritancy also increases.

EXAMPLE 5

The process described in example 2 is repeated except that the imidazoline starting material used has the following composition:
- ester: 8.9%
- monoamide: 2.3%
- imidazoline: 88.1%
- aminoethyl ethanol amine: nil The final amphoteric product thus obtained, after standing at room temperature for about 3 hours, developed a precipitate which gradually made the product opaque. However, upon heating the product to about 40° C., the opacity recedes, but reappears on cooling. A Ross-Miles test performed at 25° C. with a 0.1% active solution of said product gave a foam height of 12 cm which dropped to 9 cm after 5 minutes.

We claim:

1. A process for making an amphoteric surfactant composition having low skin irritation and low eye irritation characteristics comprising the steps of
(A) first heating an agitated mixture comprised of
(1) at least one substantially pure compound of the formula:

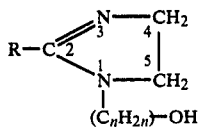

where:

R is an aliphatic radical containing from about 5 to 19 carbon atoms per molecule, and n is a positive whole number of from 2 to 4, inclusive, (2) at least one chloroacetate salt wherein the cationic portion thereof is selected from the group consisting of alkali metal, ions, and (3) water said mixture containing the equivalent of from about 1.0 to 2.5 moles of said chloroacetate salt for each mole of said formula compound, and further containing a quantity of water such that said mixture comprises from about 20 to 50 weight percent solids on a 100 weight percent total said mixture basis, said first heating being conducted at a temperature ranging from about 70° to 80° C. for a time sufficient to substantially completely consume said chloroacetate salt, (B) mixing with the resulting reactant mixture from about 1 to 2.5 moles, corresponding to the equivalent molar amount of chloroacetate salt added to said reactant mixture in step A of at least one base selected from the group consisting of alkali metal hydroxides, and then (C) secondly heating the resulting reactant mixture at a temperature of from about 70° to 80° C. at least until substantially all of the imidazoline rings present in said resulting reactant mixture have opened, thereby forming a clear aqueous solution of from about 15 to 35 weight percent linear amphoteric compounds on a 100 weight percent total solution basis.

2. The process of claim 1 wherein said formula compound is charged to the zone of said first heating as a starting composition which consists essentially on a 100 weight percent total weight basis of:

(A) from about 92 to 99.5 weight percent of said formula compound, (B) from about 0.5 to 3 weight percent of aminoethyl lower alkanol amine, (C) from 0 to about 2 weight percent of byproduct ester, and (D) from 0 to about 5 weight percent of an aliphatic monoamide.

3. The process of claim 2 wherein said starting composition contains, on a 100 weight percent total basis:

(A) from about 97 to 99.5 weight percent of said formula compound, wherein n is 2, (B) from about 0.5 to 1 weight percent of aminoethyl ethanol amine, (C) from 0 to about 0.5 weight percent of said ester, and (D) from 0 to about 2 weight percent of said monoamide.

4. The composition produced by the process of claim 1 said composition having a foamability of at least about 16 centimeters by the Ross-Miles test procedure, said composition being further characterized by (A) having a stability such that said composition remains a clear solution after at least about 7 days of storage at 5° C., (B) containing an amphoteric compound having a tertiary amide function in which one of the substituents on the tertiary nitrogen is either —CH$_2$CH$_2$OH or —CH$_2$COONa, said amphoteric compound being present in the amount of at least 25% by weight of total ampholyte, and (C) containing at least one of the linear ampholytes of the formulae:

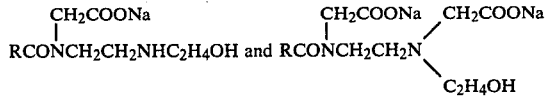

said linear ampholyte being present in the amount of at least 10% by weight of total amphoteric compounds.

5. A composition of claim 4, having a skin irritation of not more than about 1.0/8.0 on albino rabbits by the Draize et al procedure, and further having an eye irritation of not more than about 15/110.0 on albino rabbits by the Draize et al procedure.

6. A composition of claim 4 wherein n is 2.

7. A composition of claim 4 wherein R comprises lauryl.

8. A composition of claim 4 wherein a mixture of said formula compounds is employed and R is an aliphatic radical ranging from about 5 to 17 is derived from coconut oil.

9. A composition of claim 4 wherein a mixture of said formula compound is employed and R is an alkyl radical ranging from about 11 to 13.

10. The process of claim 1 wherein said chloroacetate is initially in aqueous solution before being mixed with said formula compound of formula (4).

11. The process of claim 10 wherein said chloroacetate solution and said formula compound are concurrently and continuously gradually added into the zone of said first heating at respective relative rates such that a predetermined substantially constant mole ratio within the mole ratio range above specified is maintained throughout such addition.

* * * * *